US00PP09851P

United States Patent [19]

Bost

[11] Patent Number: Plant 9,851

[45] Date of Patent: Apr. 8, 1997

[54] HIBISCUS PLANT NAMED 'BOST HYBRID NO. 3'

[76] Inventor: Georgia A. Bost, 1209 Pine Chase, Houston, Tex. 77055

[21] Appl. No.: 519,843

[22] Filed: Jun. 19, 1995

[51] Int. Cl.[6] ..... A01H 5/00

[52] U.S. Cl. ..... Plt./67.8

[58] Field of Search ..... Plt./67.8

[56] References Cited

U.S. PATENT DOCUMENTS

P.P. 835 5/1949 Hemming ..... Plt./67.8
P.P. 4,271 6/1978 Darby ..... Plt./67.8
P.P. 5,209 3/1984 Darby ..... Plt./67.8
P.P. 7,608 7/1991 Winter ..... Plt./67.8
P.P. 9,555 5/1996 Morrison ..... Plt./67.8

*Primary Examiner*—James R. Feyrer
*Attorney, Agent, or Firm*—Martin L. McGregor

[57] ABSTRACT

An herbaceous perennial Hibiscus plant named 'Bost Hybrid No. '3' having numerous large polypetalous flowers with rich red color, separate petal arrangement, a dark, 3-zoned red eye, buds of darker red, and moderate to large-sized well-branched, upright plants with three-lobed leaves of dark green color.

1 Drawing Sheet

HISTORICAL NOTE

As of August 1966, there are a total of 20 plant patents granted for the species Hibiscus in the United States of America. The earliest patented hibiscus plant (U.S. Plant Pat. No. 835), identified in the records simply as 'Mallow', was selected from a population having within its genetic background *Hibiscus laevis* (formerly *militaris*), *H. coccineus,* and *H. moscheutos*. This early improved plant was characterized by having smooth, deeply cut leaves, as attaining shrub height of medium size, of having medium sized (6–8 inch) flowers with deep red, imbricated flower petals and by being adapted for culture in the temperature zone.

Within the remainder of the existing patents, 10 are *H. "rosa-sinenis"* types developed by Frank Moser; three more are also *H. rosa-sinensis* varieties, developed by Roberta Ludick; and one is a variegated sport of *H. paeoniflorus,* selected by Harold Hillis. All plants in this group of patents are developed from tropical, mostly pan-Pacific species that do not survive unprotected north of USDA Zone 10.

The novel plant invention described herein is developed from the suite of perennial hibiscus species belonging to Hibiscus Section Meunchhusia (O. J. Blanchard, 1976; P. A. Fryxell, 1988) that are native to the continental United States. There are four recognized species in this Section (*H. coccineus, H. dasycalyx, H. laevis,* and *H. moscheutos*) one of which has several recognized subspecies: *H. moscheutos, H. m. palustris,* and *H. m. grandiflorus.* The other species of Hibiscus native to the conterminous U.S. and Hawaii are not genetically compatible with these four species.

All species of Hibiscus in Section Meunchhusia are wetland plants and, although tolerant of even severe draught (via semi-dormancy), perform best under adequate moisture conditions. They tolerate—rather than require—saturated soil and/or standing water conditions and compete best in the wild on the borders of water bodies where periodic fires reduce competition from woody species. Consequently, they make excellent low-maintenance border plantings around water features and grow well in all climates where adequate rainfall and/or irrigation is available. As a general rule, the farther north the planting, the less water is required and the shorter plant will be at maturity.

There are currently only six patented varieties of this type of hibiscus: 'Mallow' (Hemmings, U.S. Plant Pat. No. 835), 'Lady Baltimore' (Darby U.S. Plant Pat. No. 4,271), 'Anne Arundel' (Darby U.S. Plant Pat. No. 5,209), 'Sweet Caroline' (Winters U.S. Plant Pat. No. 7,608), 'Quatro Rojo' (U.S. Plant Pat. No. 9,311), and 'Pink Wonder' (Morrison, U.S. Plant Pat. No. 9,555). The first four of these plants were developed from East Coast USA populations of Hibiscus species (or subspecies) *H. moscheutos. H. moscheutos* ssp. *palustris,* and/or *H. laevis,* in various combinations with the Florida species, *H. coccineus.* The sixth was developed from *H. moscheutos, H. m. palustris* and *H. laevis,* 'Quatro Rojo' was developed from progeny of crosses made with a population of *H. laveis* native to Texas, in various combinations with *H. coccineus* and *H. moscheutos* ×'Southern Belle'; the latter was developed from U.S. native hibiscus by Japanese breeders many years ago and marketed in the USA, originally through seed catalogs. 'Southern Belle' is dominated by *H. moscheutos* characteristics.

The general growth habit of Section Meunchhusia hibisci is characterized by long, straight, light-weight canes which arise annually from a perennial crown. Once established, crowns generally bud two to three—more rarely, four—new shoots from the base of each of the preceding season's canes. Side branching occurs in the upper half to one-third of the cane (depending on species dominance), given sufficient length of growing season, but generally is not initiated until first bud set has occurred. Forking of canes occurs only if the green cane is cut or broken off.

Crowns frequently go through cycles of cane production that are a function of the age of the crown and the amount of crowding in the center of the crown. Typically, new canes are more abundant on the outside of the crown, until enough space has developed in the center to once again allow central cane growth. Plants can be propagated effectively either from crown division or from cuttings; for either method, rooting hormone is optional.

Cane production is typically much more vigorous (in both size and number) in hybrids than in the native specimens, all other factors being equal. In general, a new seedling will produce only one cane due to the time it takes for the plant to mature enough to begin flower budding. Second year crowns generally break dormancy with 2–3 canes, but may produce more given a sufficiently long growing season. Third year crowns typically produce 6–9 canes, and so on. Number and vigor of canes is also dependent on spacing of the individual specimens and the size of the container in which it is grown, as well as length of growing season where grown, and the genetic background of the parental stock from which the cultivar was developed. Plants become severely stunted when container size is too small for the crown size. A well developed crown will frequently outweight its canes.

Spacing of leaves, internodal length and leave shape are a function of species genome, as is bloom onset and distribution, abscission point, and presence or absence of foliage on bloom pedicels. However, these characters in hybrids show a wide range of intermediate characters and may or may not be distinctive for a given hybrid type.

Overall plant presentation ranges from *H. moscheutos* on one extreme, with an essentially spherical presentation (consisting of relatively short canes and widely-spaced but large, cordate leaves), to *H. coccineus* on the other extreme, with an essentially vase-shaped or V-shaped presentation of 5-lobed, highly-dissected, Cannabis-like leaves. *H. laevis* and *H. dasycalyx* have the shortest internode size with leaves that are predominantly 3-lobed and hastate, with an essentially vase-shaped habit. *H. moscheutos* flower buds tend to produce a panicle-like effect due to the extreme fore-shortening of flowering internodes and the relatively short period of flowering for this species (1–2 months, even in Zone 9). The other three species have well-spaced flowers that follow the same rotation as the leave nodes and bloom for 2–7 months, depending on soil temperatures and frost dates for the region in which they are grown, and genetic dormancy for the region of origin.

On the average, a given flower for any of these genomes will last only one day; however, cool nights followed by cool mild day(s) commonly delay flower drop for an additional day or two, especially if fertilization has not occurred. The farther north the plants are grown, the more likely the flowers are to last more than one day. Thus, the ability of a given flower to last more than one day is not a particularly distinctive character within this group. Similarly, the more northern USDA zones will have shorter and more concise bloom periods and may frequently experience frost before "natural" dormancy begins. The regional affect on the genetic component of dormancy appears to apply primarily to the breaking of dormancy in Spring, not to winter onset.

In Zone9, dormancy almost always occurs before frost, although some plants have still been observed to bloom as late as the end of January, during especially mild winters. Dormancy appears to be triggered by soil temperature, but also shows a strong genetic component related to the climatic region of the source genome. Dormancy or semi-dormancy can also be triggered by severe draught. A normal winter-triggered dormant period seems to be beneficial for this group of Hibiscus, as specimens grown in tropical climates or in heated greenhouses year-round loose vigor, are less resistant to disease and pests, and eventually die prematurely (five years or less).

The average life span of the perennial crowns of these species and their hybrids has not, to our knowledge, been documented. Anecdotal evidence suggests crown life-spans of more than 25 years and, barring catastrophic events or disease, could be more than 100 years.

BACKGROUND OF THE NEW PLANT

The breeding program which produced the novel plant invention described herein and named 'Bost Hybrid No. 3' extended over a period of some 9 years. 'Bost Hybrid No. 3' originated as a seedling selected from progeny of cross pollination between (1) a breeding line derived from crossing the commercially available *H. moscheutos* var. "Southern Belle" and *H. laevis* BOST×® selection 'Houston-White'; (2) a breeding line derived from crossing *H. laevis* BOST×® selection 'Houston-White' and *H. coccineus;* and, (3) a breeding line derived from crossing *H. coccineus* and *H. moschuetos* var. "Southern Belle".

'Bost Hybrid No. 3' is a product of crossing Bost Hybrid 'Lady-Bird-2' (pod parent) with Bost Hybrid 'Nathan's Star' (pollen parent). 'Bost Hybrid No. 3' clearly shows characteristics of at least two of the original parent (P1) genomes used to establish this breeding program.

The objective of the breeding program which produced the novel plant of this invention was primarily to develop a plant that was suitable for inclusion in a horticultural group to be marketed as the "Fiber Series" of BOST×® agricultural and horticultural hybrids and having the following characteristics:

(a) Large plant suitable for horticultural or agricultural cultivation with good form and reliably upright habit.
(b) Decorative and productive foliage of a pleasing shade of green and well-placed flowers/pods suitable for display or cropping and not shared by current landscape or agricultural varieties.
(c) Attractive, well-formed, large deep red flowers that are distinctive for the color and form, that are well-posed on the plant and that remain open for most of the day (two days incooler weather).
(d) Prolific production of relatively large, well seeded pods for use the production of in agricultural product.

SUMMARY OF THE INVENTION

The present invention comprises a new and distinct cultivar of herbaceous perennial Hibiscus hybrid hereinafter referred to by the cultivar name 'Bost Hybrid No. 3°. It was a seedling selected by Georgia A. Bost in July of 1992 from a seedling population grown at her nursery, The Village Botanica, Inc., at 7500 Westview Drive, Houston, Tex. She is the owner of the mother plant and clones and controls all propagation of it. The new plant produced its first flower in the summer of 1992 and, because of the size and shape of the plant and the coloring of the flower, its attractive foliage and vigorous habit, was selected for reproduction and testing. Asexual propagation of this new plant by cuttings was carried on at The Village Botanica, 7500 Westview Drive, Houston, Tex. in (year) and at JJL Greenhouses, Inc., 1449 Brittmoore, Houston, Tex.) in (1991–1994) under exclusive contract to The Village Botanica, Inc. Observation of the asexual progeny of the original plant has demonstrated that this new and distinct variety has fulfilled the objectives and that its distinctive characteristics are firmly fixed and hold true from generation to generation vegetatively propagated from the original clone.

The new and distinct cultivar is of value for its floral display, produced from late May until late November (or frost), depending upon USDA zone in which it is cultured, environmental conditions and culture methods; for the landscape value of the entire plant; and as a source of plant materials for commercial, horticultural and the agricultural products.

BRIEF DESCRIPTION OF THE DRAWING

This new cultivar of perennial Hibiscus is illustrated by the accompanying full color photographic drawing which shows.

DETAILED DESCRIPTION OF THE NEW PLANT

Figure 1:
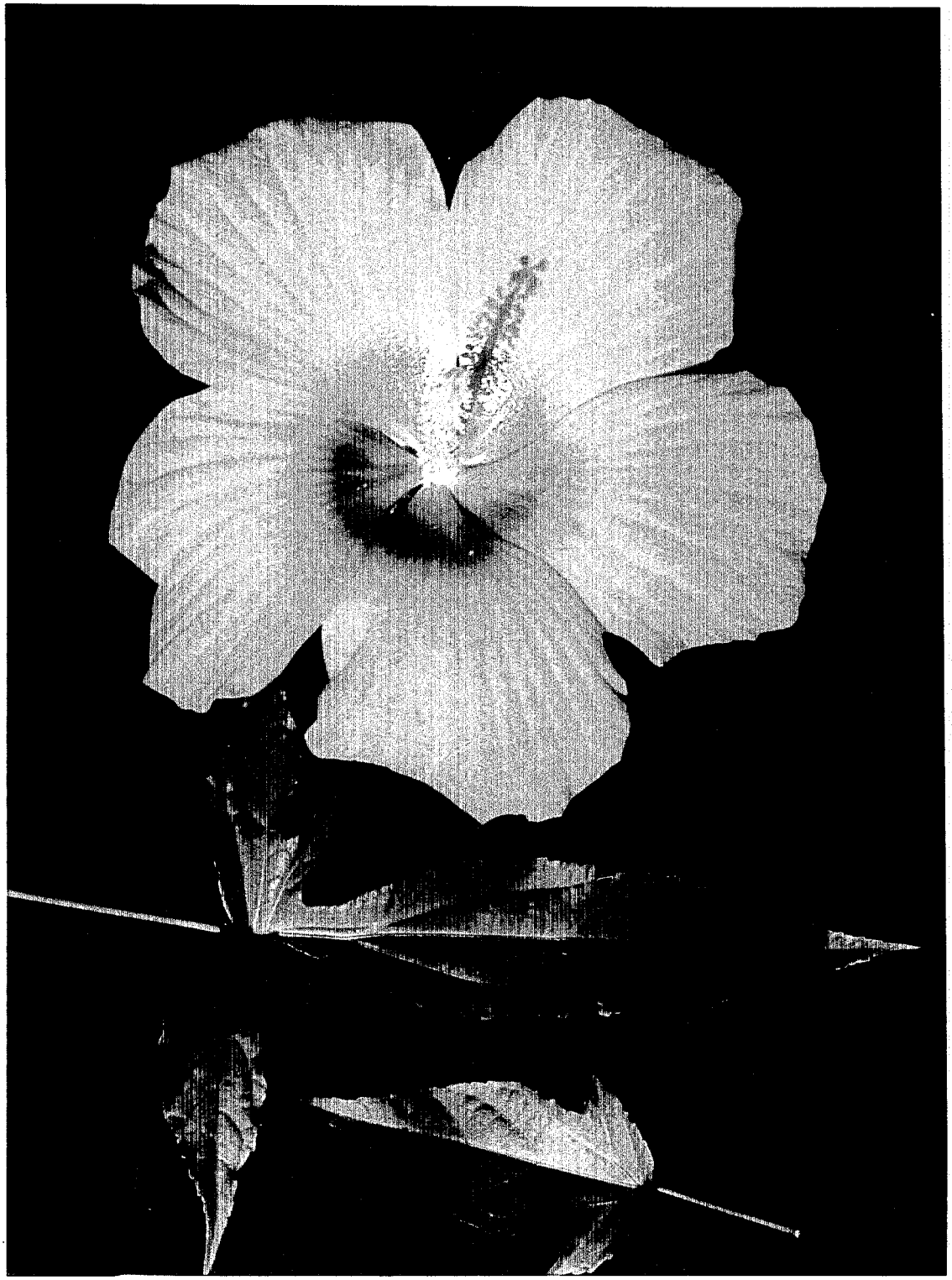
FIG. 1—a fully opened flower and some typical leaves, the colors being as true as can reasonably be done by conventional photogrpahic procedures. Bud form and texture are not distinctly different from many other varieties of hybrids in this group of Hibiscus, or from other BOST×® hybrids of this type. The overall plant form is adequately describe in the text.

The following is a detailed description of the new variety, color terminology being in accordance with The Royal Horticultural Society Colour Chart (indicated by initials RHS-number) for the closest match or with ordinary dictionary significance.

THE PLANT

Type: Root-hardy, herbaceous perennial.

Classification: Hybrid variety of Hibiscus, Section Meunchhusia (Fryxell, 1988).

Origin: Seedling.

Parentage: Is known to be a selection from BOST×® breeding population from cross pollination between (1) a breeding line derived from crossing the commercially available *H. moscheutos* var. *Southern Belle' with H. laveis* selection 'Houston-White'; (2) a breeding line derived from crossing *H. laevis* selection 'Houston-White' with *H. coccineus;* and (3) a breeding line derived from crossing *H. coccineus* with *H. moscheutos* var. 'Southern Belle'. The pod parent is 'Lady Bird-1' and the pollen parent is 'Nathan's Star', both of which are BOST×® hybrids developed from the above breeding line.

Propagation: Holds its distinguishing characteristics through succeeding propagation by cuttings and divisions.

Form: Bushy annual growth from perennial roots, with 3–6 inch internodes on mature growth.

Mature habit: Upright and much branched, generally V-shaped in cross-section, with long canes flaring out from the root crown at about $10^{-45°}$ from vertical, forming a flared cone in 3-dimension. Side branches tend to be at about 45° angles with respect to their central canes.

Growth: Vigorous.

Foliage:

*Arrangement.*—Alternate.

*Form.*—3-lobed, incised, frequently hastate, palmately veined.

*Size.*—Average is 4–8 inches along primary vein, approx. 0.5 to 0.95 times as wide across lateral (hastate) lobes. Central lobe always larger than the individual lateral lobes. Margins—serrate. Color—top: dark green, bronzed in full sun and developing dark red veins. Color—bottom: lighter green, veins not reddened. Stipules: deciduous.

*Stem.*—Cane-like, pale green when young; blushing to dark red in full sun and in the Fall. Basal cane diameter is approximately two inches for mature plants.

Height: 7 to 10 feet.

THE FLOWER

Blooming habit.—Continuous and free blooming, late May–November (or until frost).

Corolla:

*Diameter.*—6.5 to 8 inches. The bloom is recurved, rather than flat, so the diameter is less than the sum of the length of two petals.

Shape: Deeply flared, fully open star with rounded, medium-sized petals basally and distally separated, but overlapping midway.

Involucral bracts:

*Number.*—12, each about ⅞ inches long.

*Color.*—Medium green (RHS-146D).

Calyces:

*Number of sepals.*—Five. Shape deeply dissected (split at 0.5 inch from base), arrow-shaped, with pronounced apical point at about 1.25 inches from base.

*Color.*—Matt green (RHS-146D to 144D), streaked with dark maroon (RHS 187B) in full sun.

Filaments:

*Color.*—Pink (RHS-54D).

Anthers: Light brown in color.

Stamens: Numerous, clustered at about equal distance between stigmata and base of style ~1.375 inches total.

Stigma:

*Color.*—Red (~RHS-53A). Essentially no peduncle, stigma pedicels. Providing the total length of the stigma structure. Pedicels and pads are the same color, total size is 0.5 inches.

*Number.*—Five, rounded discoid, hairy.

Staminal column:

*Length.*—2.25 inches, centrally antheriferous, lower 0.375 inches pure white. Area of style that is anthiferous is streaked with pink and red (~RHS-54A). Base of pistil or very center of throat: white (RHS-155C), with small white "wings" at one side of base of each lobe of the eye (left or right, depending upon rotation of the individual flower).

Pollen: Medium yellow (~RHS20B).

Petalage:

*Shape.*—Ovate, very slightly asymmetrical, apical point right or left of center, depending upon rotation of the individual flower.

*Size.*—3.5 to 4 inches (base of style to tip of petal) by 3 to 3.5 inches wide, depending upon cultural conditions and the temperature of the preceding night.

*Aspect.*—Central one-third satiny outer two-thirds translucent.

*Texture.*—Moderately thick, about the weight of broadcloth.

*Color.*—Center eye zone: dark shindy red (RHS-46D), grading in two zones to very dark purplish red (RHS 187B) and back to dark red (RHS-46D). Front of petal: Color does not exactly match any of the RHS color strips because of subtle gradations of red across the petal, but colors fall between RHS-58A and RHS53B. Back of petal: essentially the same as the front, except the area corresponding to the eye on the front is white on the back. The overall effect is of a large petalled, slightly recurved rich red star with a deep red, zoned eye.

Flower: Numerous, elegant; individual flowers last one day, two days in cooler weather.

Peduncle: 3 to 5 inches; medium thickness; very stiff.

GENERAL CHARACTERISTICS AND CULTURE

Blooming period: Late May to November (or frost) on the Texas Gulf Coast (Zone 9), July or early August to frost in cooler zones. From the onset of the blooming period the plant is seldom without flowers.

Hardiness: Root hardy to at least zone 5 (further North is well mulched). Dormancy is apparently triggered by soil temperatures rather than by photoperiod. Research at Michigan State indicates that Hibiscus in this group are day-neutral bloomers.

Breaking action: Very tough. Immature stems bend and regrow.

Rooting: Excellent. Hormone optional, especially under mist.

Growth regulator: Not required. Optional for holding in pots for commercial nurseries.

Shipping tolerance: Excellent, especially as liners or at any size when dormant. Best shipped in single rows on tiered shelves when dormant.

I claim:

1. A new and distinct cultivar of Hibiscus plant, as shown and described.

* * * * *